(12) United States Patent
Sheila-Vadde et al.

(10) Patent No.: US 7,948,233 B2
(45) Date of Patent: May 24, 2011

(54) OMNIDIRECTIONAL EDDY CURRENT ARRAY PROBES AND METHODS OF USE

(75) Inventors: Aparna Chakrapani Sheila-Vadde, Karnataka (IN); Ui Won Suh, Cincinnati, OH (US); Changting Wang, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 358 days.

(21) Appl. No.: 12/246,637

(22) Filed: Oct. 7, 2008

(65) Prior Publication Data
US 2010/0085045 A1    Apr. 8, 2010

(51) Int. Cl.
  *G01N 27/72*  (2006.01)
  *G01N 27/82*  (2006.01)
  *G01R 33/12*  (2006.01)
(52) U.S. Cl. ........................ 324/242; 324/239
(58) Field of Classification Search .............. 324/239, 324/242
See application file for complete search history.

(56) References Cited

U.S. PATENT DOCUMENTS

| | | | |
|---|---|---|---|
| 3,875,502 A | 4/1975 | Neumaier | |
| 3,876,932 A | 4/1975 | Domon et al. | |
| 4,310,821 A | 1/1982 | Frances | |
| 4,706,020 A | 11/1987 | Viertl et al. | |
| 5,015,951 A | 5/1991 | Melcher | |
| 5,047,719 A | 9/1991 | Johnson et al. | |
| 5,442,286 A | 8/1995 | Sutton, Jr. et al. | |
| 5,659,248 A | 8/1997 | Hedengren et al. | |
| 5,793,206 A | 8/1998 | Goldfine et al. | |
| 6,188,218 B1 | 2/2001 | Goldfine et al. | |
| 6,344,739 B1 | 2/2002 | Hardy et al. | |
| 6,424,151 B2 | 7/2002 | Kawata et al. | |
| 6,888,347 B2 | 5/2005 | Batzinger et al. | |
| 7,015,690 B2 | 3/2006 | Wang et al. | |
| 2004/0257072 A1 | 12/2004 | Samson | |
| 2005/0007106 A1 | 1/2005 | Goldfine et al. | |

FOREIGN PATENT DOCUMENTS

| JP | 7244027 | 9/1995 |
|---|---|---|
| JP | 8334498 | 12/1996 |

*Primary Examiner* — Reena Aurora
(74) *Attorney, Agent, or Firm* — Penny A. Clarke

(57) ABSTRACT

Omnidirectional eddy current array probes for detecting flaws in a conductive test object generally includes semicircular wave shaped continuous drive lines in two rows disposed in two layers that are multiplexed for omnidirectional inspection without blind spots. The semicircular wave shaped continuous drive lines are superimposed to form pseudo-circular drive lines, wherein each row of drive lines is offset laterally by a distance preferably equal to a quarter wavelength of the wave pattern. For only parallel and perpendicular flaws, the drive multiplexing is not needed and each row will have only one set of drive lines. In alternate embodiments, there can be square-shaped, oval shaped, rectangular-shaped or other shaped wave patterns as well. Also disclosed are methods for sensing surface flaws and compensating their response.

19 Claims, 7 Drawing Sheets

OMNIDIRECTIONAL EDDY CURRENT ARRAY PROBES AND METHODS OF USE

BACKGROUND

This disclosure generally relates to probes and methods for non-destructive evaluation, and more specifically, to eddy current probes and methods for non-destructive inspection of conductive test objects.

Industrial processes often use non-destructive examination to test and/or inspect an object without damaging the object. For example, aircraft components formed of conductive materials often need to be inspected for surface flaws such as cracks. One such method for non-destructive testing of conductive materials for flaws is eddy current inspection. Eddy current inspection is accomplished with probes configured to have current flow in a drive coil line, which results in an electromagnetic field being created. The electromagnetic field induces eddy currents on the metallic test object. The eddy currents so induced in turn generate a secondary magnetic field, which creates a potential difference in sensors (coils or other transducers), whose outputs may be analyzed for flaw detection. If there are no detectable flaws, then the sensors should output uniform voltage. If there are detectable flaws, then the current flow within the test specimen is altered, thereby altering the signals induced in the sensors.

Typical eddy current inspection methods generally assume the orientation of the surface anomaly is known and the probes are designed accordingly. However, in several situations such as, for example, the flat area of an engine disk, cracks can occur in different orientations. From productivity concerns, it is desirable to use array probes to inspect larger surface areas more efficiently. However, current eddy current array probes usually are made up of discrete elements and typically have regions through which small flaws can pass through with low detectability. For example, a prior art eddy current array probe utilizes for each channel, rectangular sense coils offset in the x and y directions with a drive coil encircling each sense coil. However, flaws parallel to the array length that are close to the size of the gap between elements can pass through with low sensitivity. Compensation of the responses from this probe is oftentimes difficult due to the complicated footprints. Another problem is that the high number of drive vias can result in low fabrication yields. Arrays of circular coils have been used by continuously switching the elements in the array to transmit and receive mode. However, the flaw sizes that can be detected using this type of configuration would be larger than the size of one coil. Moreover, there is no consideration as to how to use this probe for flaws that are at angles other than about 0 (i.e., parallel direction to array length) and about 90 degrees (i.e., perpendicular to array length).

Accordingly, it would be desirable to have an improved eddy current probe and methods for robust inspection of flaws regardless of its orientation.

BRIEF DESCRIPTION OF THE INVENTION

The shortcomings of the prior art are overcome and additional advantages are provided through an omnidirectional eddy current array probe for detecting flaws at different orientations in a conductive test object. In one embodiment, the omnidirectional eddy current probe comprises a first row comprising a first drive line (which may consist of multiple turns) disposed in a first layer having a first wave pattern with a first peak and a first trough operative to induce a first eddy current in the conductive test object, and a second drive line disposed in a second layer having a second wave pattern with a second peak and a second trough operative to induce a second eddy current in the conductive test object, wherein the first drive line is superimposed over the second drive line; at least one additional row identical to the first row, wherein the at least one additional row is offset from the first row; and a sensing portion disposed proximate to the first and second drive lines of the first row and the at least one additional row operative to sense the eddy current in the conductive test object and output a signal indicative of the sensed eddy current. In one embodiment, the first peak is aligned along a scanning direction over the second trough and the second peak is aligned along the scanning direction over the first trough, with the drive lines in the two layers multiplexed.

In another embodiment, an eddy current probe without drive line multiplexing for detecting parallel and perpendicular flaws in a conductive test object comprises a first row comprising a drive line having a semi-circular wave pattern operative to induce an eddy current in a conductive test object; at least one additional row comprising a drive line having a semi-circular wave pattern operative to induce an eddy current in a conductive test object, wherein the first row is offset from the at least one additional row; and a sensing portion disposed proximate to the drive lines of the first and second rows operative to sense the eddy current in the conductive test object and output a signal indicative of the sensed eddy current.

A method for sensing surface flaws of a conductive substrate comprises inducing first eddy currents on the conductive substrate with first drive lines formed in a first row and at least one additional row, wherein the first drive lines have a first wave pattern with a first peak and a first trough; inducing second eddy currents on the conductive substrate through second drive lines formed in the first row and the at least one additional row, wherein the second drive lines have a second wave pattern with a second peak and a second trough, wherein the first drive lines are superimposed over the second drive lines to define a continuous wave pattern in the first row and the at least one additional row, wherein each one of the at least one additional row is offset laterally from the first row; sensing the induced first and second eddy currents; and outputting a result indicative of the sensed first and second eddy currents.

Additional features and advantages are realized through the techniques of the present embodiment. Other embodiments and aspects are described in detail herein and are considered a part of what is claimed. For a better understanding of the exemplary embodiments with advantages and features, refer to the description and to the drawings.

BRIEF DESCRIPTION OF THE DRAWINGS

Referring now to the drawings wherein like elements are numbered alike in the several FIGURES.

DETAILED DESCRIPTION OF THE INVENTION

Disclosed herein are omnidirectional eddy current array probes and non-destructive methods for detecting flaws in/on conductive objects and/or substrates. Unlike the prior art, the omnidirectional eddy current array probes disclosed herein use complementary and symmetrical drive lines disposed in two or more rows and layers in a continuous manner to detect flaws at different orientations without blind zones (i.e., less sensitive zones). Although circular symmetry is shown and generally discussed herein, other shapes are contemplated, e.g., square, oval, rectangular, and the like. In one embodiment, the omnidirectional eddy current array probe employs four semi-circular wave shaped continuous drive lines in two or more rows disposed in two or more layers that are multiplexed for omnidirectional inspection without blind spots. In one embodiment, each row is offset laterally from an adjacent row by a distance equal to a quarter wavelength of the wave pattern so as to provide omnidirectional flaw detection. The lateral offset between rows ensures a minimum response for a particular crack orientation from one drive gets automatically compensated with a maximum from the drive in the next row. Multiplexing ensures that drive lines (i.e., coils) in only one layer are activated at any one instant so as to avoid non-uniformities in the eddy current distribution. In other words, the pseudo-circular and offset configuration ensures that there are no gaps between sensing elements and that a flaw is detected by one or more of the sensing elements in either the top or bottom row. It should be apparent in view of the disclosure that if only parallel and perpendicular flaws are of interest, then only one drive line is needed in each row, i.e., no drive multiplexing is needed.

Figure 1:
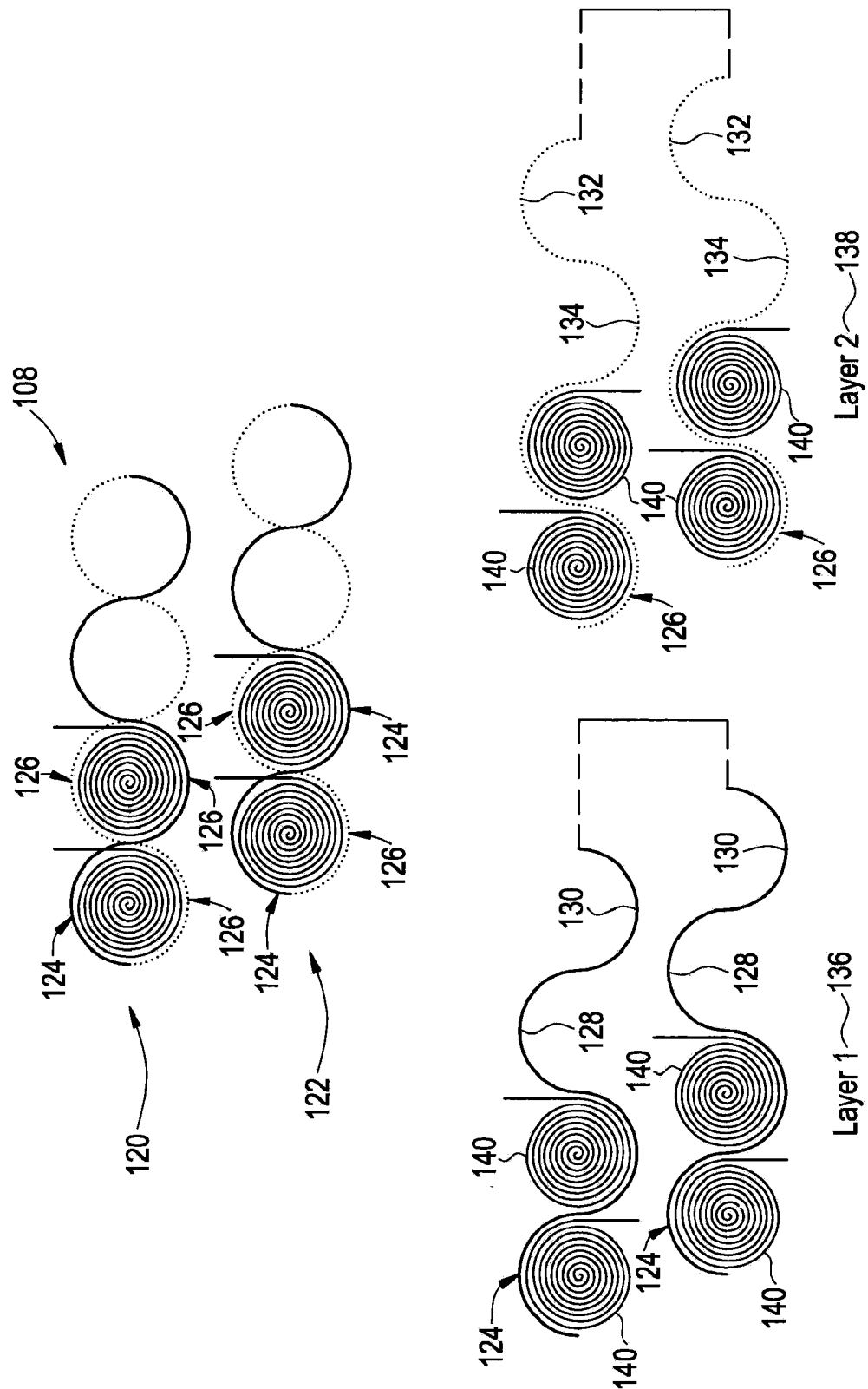
FIG. 1. illustrates an exemplary omnidirectional eddy current array probe in accordance with the present disclosure
Figure 2:
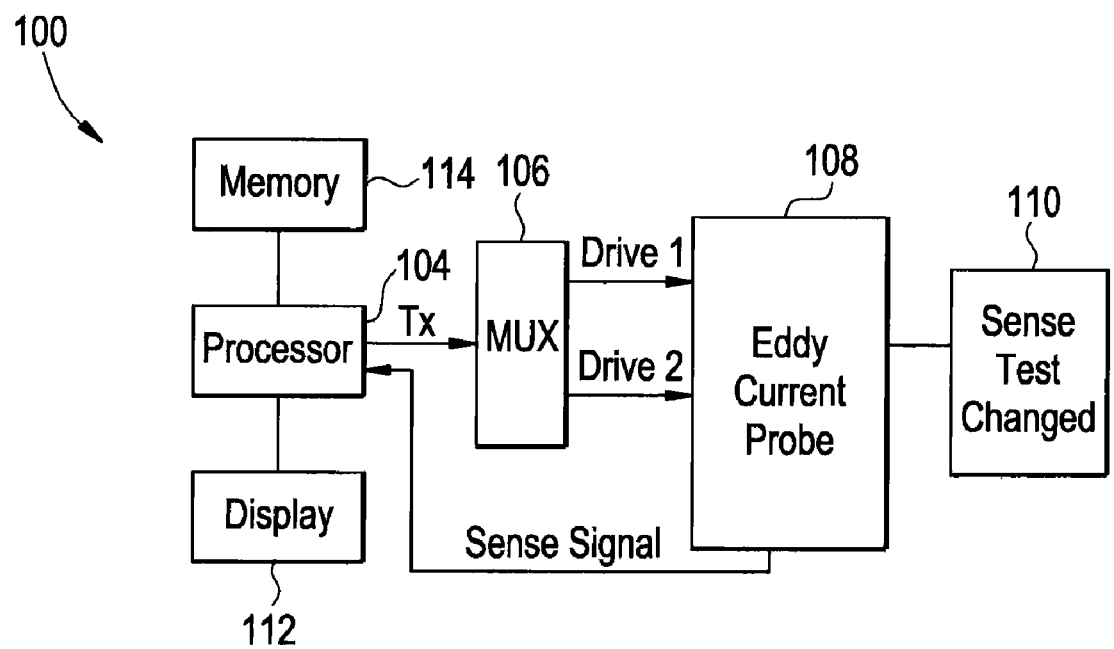
FIG. 2 illustrates an exemplary embodiment of system for omnidirectional eddy current inspection.

FIG. 1 illustrates an exemplary embodiment of an omnidirectional eddy current probe 108. The omnidirectional eddy current array probe 108 generally includes two rows 120, 122 of two drive lines 124, 126 connected through the switch multiplexer 106 (as shown in FIG. 2). Each drive line 124 or 126 within a selected row provides a semi-circular wave pattern, wherein drive line 124 can have a first wave pattern with a first peak 128 and a first trough 130 operative to induce a first eddy current in the conductive test object; and the second drive line 126 has a second wave pattern with a second peak 132 and a second trough 134 operative to induce a second eddy current in the conductive test object. The first and second drive lines 124, 126 are formed in two or more different layers 136, 138 such that when the first drive line 124 is superimposed over the second drive line 126 the first peak 128 is aligned along a scanning direction (e.g., vertically) over the second trough 134 and the second peak 132 is aligned along the scanning direction over the first trough 130. By superimposing the semicircular drive lines 124, 126 in this manner, a pseudo-circular wave pattern is formed in two rows. In one embodiment, the first row 120 is offset from the second row 122 by a distance equal to a radius of a semi-circle or one quarter of a wavelength (i.e., ninety degrees). Each of the drive lines in each row may be composed of multiple turns in the same layer or in other layers. It should be apparent that if interest is only in detection of parallel and perpendicular flaws then only one drive line is needed. As such, no drive multiplexing would be necessary.

Spiral sense elements 140 are disposed within a parameter defined by the superimposed drive lines and are offset by 90 degrees in the two rows as shown. While in one embodiment the sensing wires 140 illustrated are in a spiral shape and are placed in the middle of the pseudo-circles formed by the superimposed drive lines, the illustrated spiral sensing wires are not intended to limit what is described. In other embodiments, the sensing wires can run on both sides of the drive lines and follow alongside the drive lines, for example. The particular shape and configuration of the sensing elements is not intended to be limited. The sense signal may be configured to provide either absolute or differential output for an N-channel output where N is limited by the multiplexer capability and or the size of the array It should be apparent that the drive lines can include multiple turns, which means there will be multiple drive lines which all have the same shape as the first that has been described and need not be confined to two layers. These drive lines may be wired in series or parallel as the requirement demands.

An exemplary embodiment of such a system 100 for testing for flaws on conductive objects is illustrated in FIG. 2. A processor 104 is in communication with memory 114, a display 112, such as, for example, a monitor, and a multiplexer 106. The processor 104 sends a drive signal to the multiplexer 106, which in turn sends the drive signal to the eddy current probe 108 via drives 1 and 2. In an alternate embodiment, the processor 104 sends the drive signal directly to the probe 108 such as may be desired for detection of only parallel and perpendicular flaws as will be discussed in greater detail below. The probe 108 is configured to send a sense signal back to the processor 104. The probe 108 may also send a signal to a "sense test changed" watcher 110.

Figure 3:
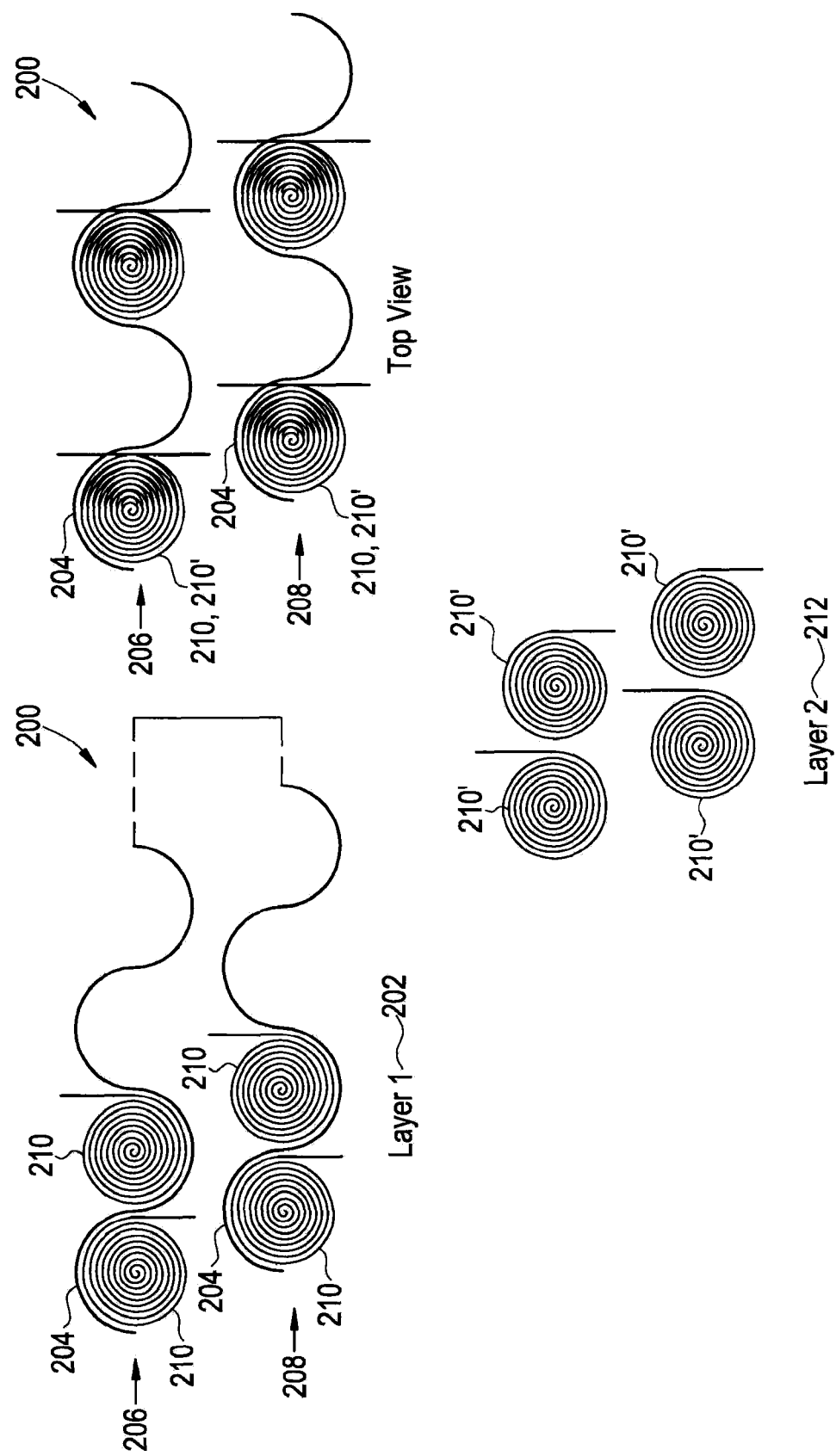
FIG. 3 illustrates an exemplary omnidirectional eddy current probe in accordance with another embodiment of the present disclosure.
Figure 4:
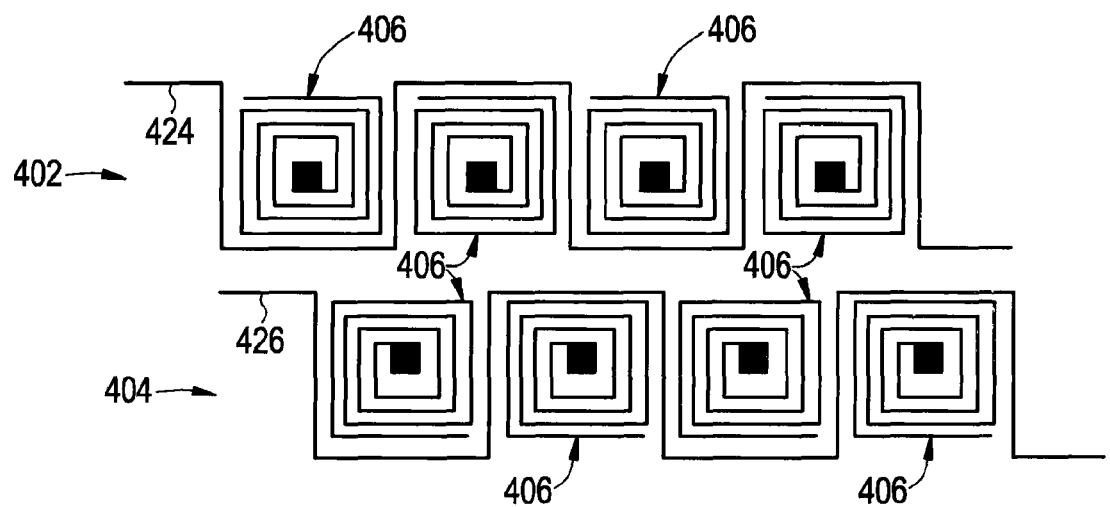
FIG. 4. shows the embodiment with a square wave shape for the drive line

FIG. 3 illustrates an eddy current probe 200 without drive multiplexing in accordance with another embodiment that is sufficient when all of the flaws encountered will either be parallel or perpendicular (i.e., at about zero degrees or about ninety degrees). The first layer 202 includes a drive line 204 which forms two rows 206, 208 of semi-circles in a wave-like pattern. In alternate embodiments, more rows may be present. Sensing elements 210 are disposed proximate to each semi-circular wave pattern of the drive line. In an exemplary embodiment, the sensing elements 210 are spiral shaped wires. The positioning and shape of the sensing elements 210 is not intended to be limited and may also, for example, appear on both sides of the drive line and may appear in many shapes. The second layer 212 has similar spiraling sensing elements 210' to provide more sense turns. The second layer can be avoided if less number of turns is needed: likewise, it is possible to have sense turns in more than two layers as well, if more number of turns are required. A top view of the sensor 200 shows that the sensing elements 210' in the second layer 212 also fit inside the semi-circles, superimposed over the corresponding sensing elements 210 in the first layer 202. When only zero degree and ninety degree flaws are sought, pseudo-circular drive lines are not necessary because two rows of semi-circular drive lines will be sufficient to determine if a flaw is present. Instead of semi-circular drive lines, it is possible to have square and/or rectangular wave shaped drive lines and sense lines conforming to the drives, either spiral or otherwise. By way of example, each row is offset and includes drive lines 424, 426 that are square wave patterns as shown in FIG. 4. In one embodiment, the sensing elements 406 can have a square spiral shape and are disposed proximate to the drive lines as shown.

Figure 5:
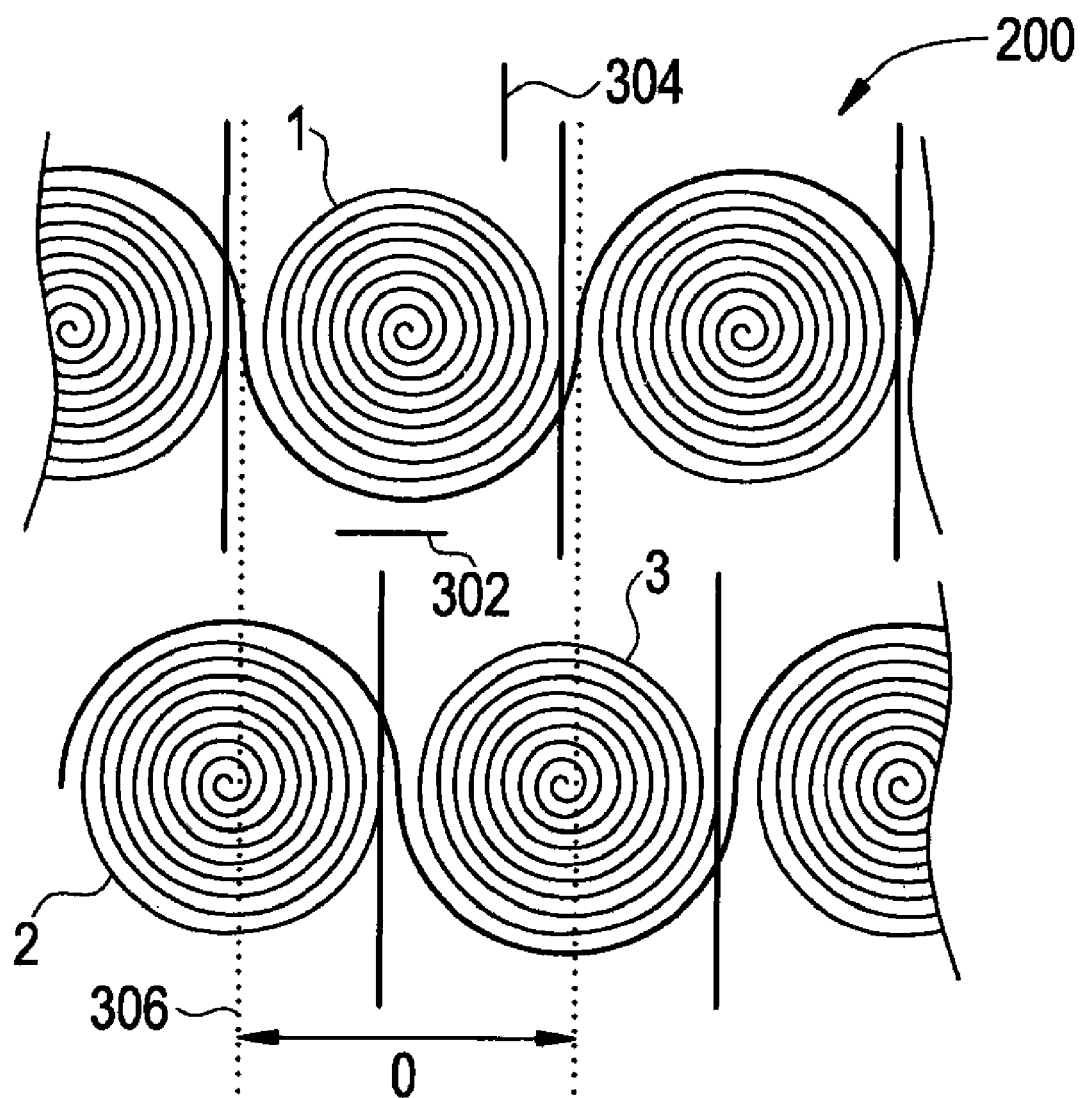
FIG. 5 illustrates three elements in two rows of an omnidirectional eddy current array probe configured for detecting parallel and perpendicular flaws.

FIG. 5 illustrates an exemplary embodiment of an eddy current probe 200 configured for detecting parallel and perpendicular flaws, e.g., the eddy current probe of FIG. 3. The parallel flaw is generally designated by reference numeral 302 and the perpendicular flaw by 304 as shown. Elements 1, 2 and 3 of the probe define a zone 306, the footprint from which is representative of the response of the array. The footprint captures the response of the flaws at different potential locations along the length of the array. It is desired to have the same response at all locations and for this, compensation schemes are typically involved to compensate the flaw response based on location.

Figure 6:
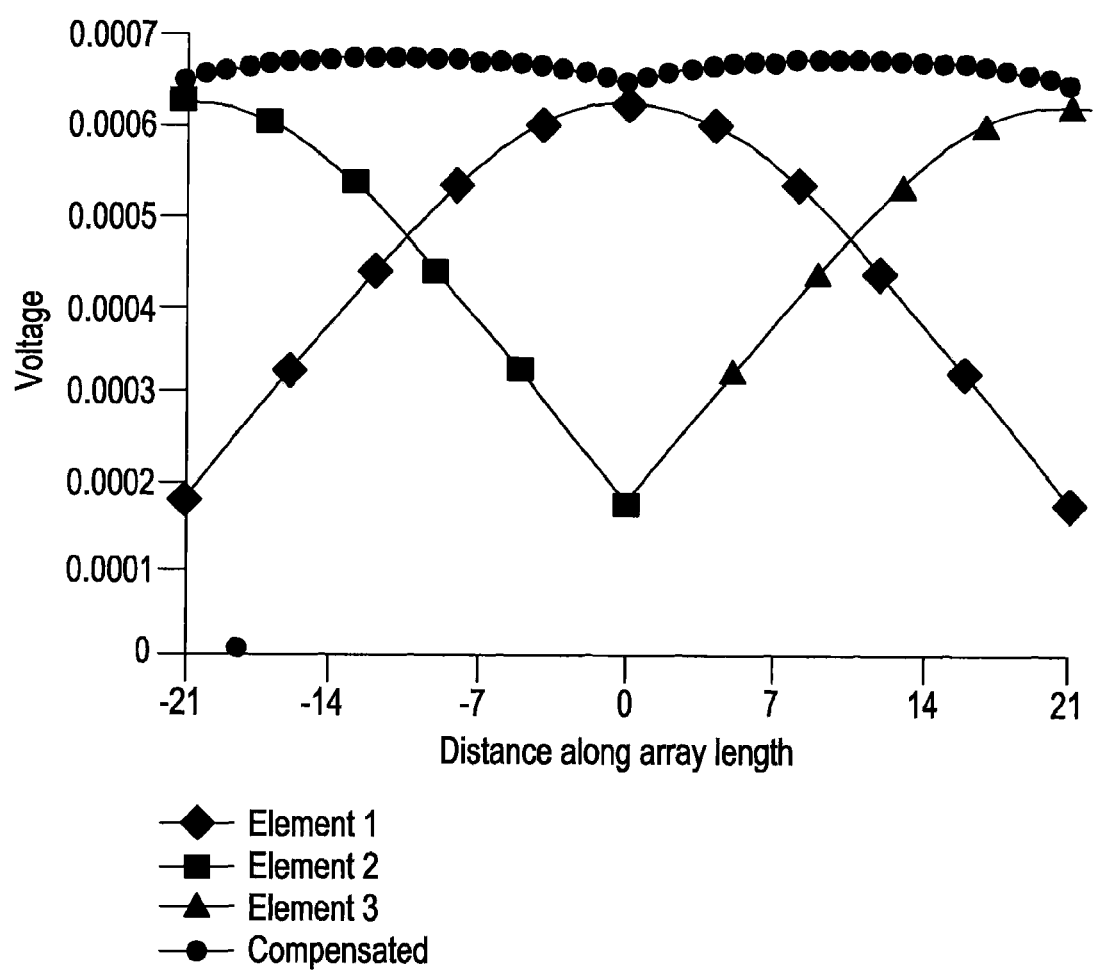
FIG. 6 graphically illustrates voltage as a function of distance for a perpendicular flaw using the eddy current probe configuration of FIG. 5.
Figure 7:
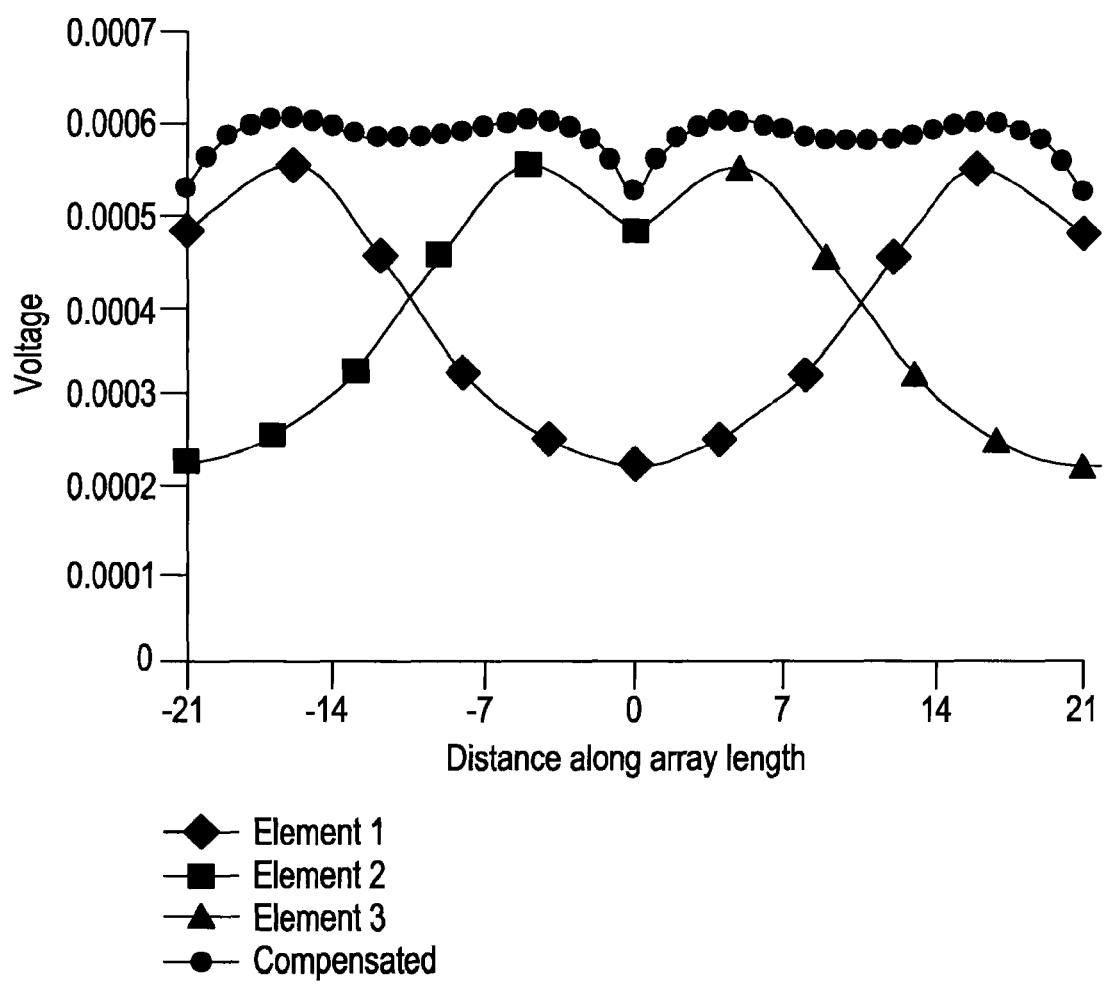
FIG. 7 graphically illustrates voltage as a function of distance for a parallel flaw using the eddy current probe configuration of FIG. 5.

FIGS. 6 and 7 graphically illustrate voltage as a function of distance along the eddy current probe for the perpendicular crack 304 and the parallel crack 302, respectively, for the three elements, 1, 2, and 3. Also, shown is a compensated plot that is the RSS or the square root of the sum of the squares as an example, which is one of the different compensation schemes possible. The compensated plot is close to being a flat response. Ideally, a compensated plot should be flat, so that a flaw would give the same voltage regardless of where the flaw crosses the drive lines. If the compensated voltage is consistent, then an accurate estimation about the size of the crack can be made. Moreover it is preferable to have the same compensation scheme work regardless of crack orientation. The Max/Min ratio, which is the ratio of the maximum value to the minimum value of the compensated response, is one way to quantify the integrity of the compensation scheme. The ideal value is unity for a perfectly flat response. As shown, the compensated responses, which used a square root of the sum of squares scheme, are seen to be relatively flat with the Max/Min ratios close to unity indicating minimal non-uniformity in sensitivity. Advantageously, the symmetry in the current eddy current probes permit the same compensation scheme to be used for both perpendicular and parallel flaws.

The technical effects and benefits of exemplary embodiments include scanning metallic objects for flaws of any direction. Advantageously, the omnidirectional eddy current probes as disclosed herein are scalable for detection of relatively small flaws. The symmetry in the design significantly simplifies the compensation technique and makes it independent of flaw orientation. For example, suitable compensation techniques include square root of the sum of squares (RSS), max of absolute, and sum of absolute of the response of two adjacent channels. Still further, the eddy current probes also address the issue of low fabrication yields by eliminating vias in the individual drive elements.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An omnidirectional eddy current array probe for detecting one or more flaws in a conductive test object, comprising:
a first row comprising a first drive line disposed in a first layer having a first wave pattern with a first peak and a first trough operative to induce a first eddy current in the conductive test object, and a second drive line disposed in a second layer having a second wave pattern with a second peak and a second trough operative to induce a second eddy current in the conductive test object, wherein the first drive line is shifted from and superimposed over the second drive line, wherein the first and second drive lines are multiplexed;
at least one additional row identical to the first row, wherein the at least one additional row is offset from the first row arranged such that the wave patterns of the first row complements the wave patterns of the at least one additional row; and
a sensing portion disposed proximate to the first and second drive lines of the first row and the at least one additional row operative to sense the eddy current in the conductive test object and output a signal indicative of the sensed eddy current.

2. The omnidirectional eddy current array probe of claim 1, wherein the first peak is aligned along a scanning direction over the second trough and the second peak is aligned along the scanning direction over the first trough.

3. The omnidirectional eddy current array probe of claim 1, wherein each row is offset laterally by a distance equal to a quarter wavelength of the wave pattern.

4. The omnidirectional eddy current array probe of claim 1, wherein the drive lines of the first and second rows comprises one or more turns and are disposed in one or more layers and the sensing portion comprises sensing elements disposed in one or more layers.

5. The omnidirectional eddy current array probe of claim 1, wherein the sensing portion comprises a plurality of spiral shaped sensing elements in one or more layers and is configured in an absolute or a differential mode.

6. The omnidirectional eddy current array probe of claim 1, wherein the first drive lines and the second drive lines are semi-circular wave shaped and when superimposed form continuous circular wave patterns in the first row and the at least one additional row.

7. The omnidirectional eddy current array probe of claim 1, wherein the sensing portion comprises sensing elements on either side of the drive lines or surrounded by and generally conforming to the continuous wave pattern defined by the first and second drive lines of the first row and the at least one additional rows and can be configured in an absolute or a differential mode.

8. The omnidirectional eddy current array probe of claim 1, further comprising a multiplexer in operative communication with the first and second drive lines of the first row and the at least one additional rows so that a drive signal alternates between being sent through the first drive lines in the first layer and the second drive lines in the second layer.

9. The omnidirectional eddy current array probe of claim 1, wherein the eddy current probe employs a common compensation scheme regardless of flaw orientation.

10. The omnidirectional eddy current array probe of claim 1, wherein the first drive lines and the second drive lines when superimposed form continuous square or continuous oval or continuous rectangular shaped wave patterns in the first row and the at least one additional row.

11. The omnidirectional eddy current array probe of claim 1, wherein the first row and the at least one additional row are combined into a single row in different layers with multiplexed drive lines.

12. An eddy current array probe without drive multiplexing for detecting parallel and perpendicular flaws in a conductive test object, the eddy current array probe comprising:
a first row comprising a drive line having a wave pattern operative to induce an eddy current in a conductive test object;

at least one additional row identical to the first row operative to induce an eddy current in a conductive test object, wherein the first row is offset from the at least one additional row; and a sensing portion disposed proximate to the drive lines of the first and second rows operative to sense the eddy current in the conductive test object and output a signal indicative of the sensed eddy current, wherein the wave pattern has a semi-circular shape, and wherein the first row is offset from the at least one additional row by a distance equal to a radius of the semi-circular wave patterns or a quarter wavelength of the wave patterns.

13. The eddy current array probe of claim 12, wherein the first drive lines and the second drive lines are square wave shaped or rectangular wave shaped in the first row and the at least one additional row.

14. The eddy current probe of claim 12, wherein the eddy current probe employs a common compensation scheme for different flaw orientations.

15. An eddy current probe without drive multiplexing for detecting parallel and perpendicular flaws in a conductive test object, the eddy current array probe comprising:
   a first row comprising a drive line having a wave pattern operative to induce an eddy current in a conductive test object;
   at least one additional row identical to the first row operative to induce an eddy current in a conductive test object, wherein the first row is offset from the at least one additional row; and
   a sensing portion disposed proximate to the drive lines of the first and second rows operative to sense the eddy current in the conductive test object and output a signal indicative of the sensed eddy current,
wherein the drive lines of the first and second rows comprises one or more turns and are disposed in one or more layers and the sensing portion comprises sensing elements disposed in one or more layers.

16. The eddy current probe of claim 15, wherein the sensing portion comprises spiral shaped sensing elements in one or more layers and is configured in an absolute or a differential mode.

17. An eddy current array probe without drive multiplexing for detecting parallel and perpendicular flaws in a conductive test object, the eddy current array probe comprising:
   a first row comprising a drive line having a wave pattern operative to induce an eddy current in a conductive test object;
   at least one additional row identical to the first row operative to induce an eddy current in a conductive test object, wherein the first row is offset from the at least one additional row; and
   a sensing portion disposed proximate to the drive lines of the first and second rows operative to sense the eddy current in the conductive test object and output a signal indicative of the sensed eddy current, wherein the sensing portion comprises sensing elements on either side of the drive lines or surrounded by and generally conforming to the continuous wave pattern defined by the first and second drive lines of the first row and the at least one additional rows and can be configured in absolute or differential mode.

18. An eddy current probe without drive multiplexing for detecting parallel and perpendicular flaws in a conductive test object, the eddy current array probe comprising:
   a first row comprising a drive line having a wave pattern operative to induce an eddy current in a conductive test object;
   at least one additional row identical to the first row operative to induce an eddy current in a conductive test object, wherein the first row is offset from the at least one additional row; and
   a sensing portion disposed proximate to the drive lines of the first and second rows operative to sense the eddy current in the conductive test object and output a signal indicative of the sensed eddy current,
where the first row and the at least one additional row are combined into a single row in different layers with multiplexed drive lines.

19. A method for sensing surface flaws of a conductive substrate, the method comprising:
   inducing first eddy currents on the conductive substrate with first drive lines formed in a first row and at least one additional row, wherein the first drive lines have a first wave pattern with a first peak and a first trough;
   inducing second eddy currents on the conductive substrate through second drive lines formed in the first row and the at least one additional row, wherein the second drive lines have a second wave pattern with a second peak and a second trough, wherein the first drive lines are superimposed over the second drive lines to define a continuous wave pattern in the first row and the at least one additional row, wherein each one of the at least one additional row is offset laterally from the first row;
   sensing the induced first and second eddy currents; and
   outputting a result indicative of the sensed first and second eddy currents.

* * * * *